(12) United States Patent
Mono et al.

(10) Patent No.: US 6,579,650 B2
(45) Date of Patent: Jun. 17, 2003

(54) METHOD AND APPARATUS FOR DETERMINING PHOTORESIST PATTERN LINEARITY

(75) Inventors: Tobias Mono, Poughkeepsie, NY (US); Paul Schroeder, Langebrueck (DE)

(73) Assignee: Infineon Technologies AG, Munich (DE)

( * ) Notice: Subject to any disclaimer, the term of this patent is extended or adjusted under 35 U.S.C. 154(b) by 140 days.

(21) Appl. No.: 09/792,205

(22) Filed: Feb. 23, 2001

(65) Prior Publication Data

US 2002/0117620 A1 Aug. 29, 2002

(51) Int. Cl.⁷ .................................................. G03F 9/00
(52) U.S. Cl. ............................... 430/5; 430/22; 430/30
(58) Field of Search ................................ 430/22, 30, 5

(56) References Cited

U.S. PATENT DOCUMENTS 5,853,927 A * 12/1998 Huang ..................... 430/22

\* cited by examiner

*Primary Examiner*—Christopher G. Young
(74) *Attorney, Agent, or Firm*—Slater & Matsil, LLP

(57) ABSTRACT

Method and apparatus for determining photoresist pattern linearity. The method and apparatus comprises a substrate and a measuring pattern (26) printed on the substrate comprising a series of parallel lines (37) having a line width (36) and having a pre-determined pitch. By magnifying the semiconductor wafer on which the pattern feature (34) is printed and analyzing the magnified wafer from a top down view, the linearity of the pattern feature (34) can be determined from the amount of shift in the edges of the pattern feature (34). By utilizing the method and apparatus for other pattern features, the linearity of the entire pattern can be determined.

22 Claims, 2 Drawing Sheets

METHOD AND APPARATUS FOR DETERMINING PHOTORESIST PATTERN LINEARITY

TECHNICAL FIELD OF THE INVENTION

This invention relates generally to semiconductor wafer fabrication and more importantly to a method and apparatus for determining photoresist pattern linearity.

BACKGROUND OF THE INVENTION

The process of photolithography has long been used in the semiconductor industry to produce integrated circuits. A circuit pattern is printed onto an actual semiconductor wafer using one of several methods of printing including projection printing. The production of integrated circuits involves having the designed pattern on the mask transfer into a photoresist image on the wafer as designed. Complete linearity results when the designed pattern transfers to the wafer exactly as designed for dimensions starting as low as 0.1 µm up to several hundred micrometers. However, real world processes will result in some deviations in the transfer of the pattern. One deviation that occurs is a shift between the desired dimensions in design and the actual dimensions of a given feature or features in photoresist. For example, a design pattern may consist of lines whose widths may deviate from the desired dimensions when the pattern is transferred to the wafer. If the line width deviations are known for line widths between 0.1 µm and 300 µm, the design data can be corrected in order to print photoresist lines exactly to the designed target dimension. Therefore, the knowledge of photoresist linearity is important for the functionality of the integrated circuits.

One approach for determining pattern linearity is to view a cross section of a photoresist line on a wafer through a scanning electron microscope (SEM). A wafer is cut and the features of the wafer on the pattern are magnified and viewed to determine the linearity of the pattern edge. However, this approach requires destroying the wafer and is very expensive, time consuming, and may lead to inconclusive results especially for dimensions larger than 1–2 µm because the required measurement accuracy (in the order of 0.01 µm) is not achieved for structures greater than about 2 µm in a SEM. This is so because larger critical dimensions are harder to view due to the low magnification, which is necessary to capture the whole structure. This results in larger errors in measurements.

Another approach for determining pattern linearity involves viewing the wafer from the top down through a scanning electron microscope. This approach does not destroy the wafer because the wafer is not cut or manipulated in any destructive manner. However, the approach has limited use. Generally, linearity of dimensions in the order of below 1 micron up to 1 or 1½ µm can be determined with accuracy. However, the determination of larger dimensions is subject to greater inaccuracy because of the SEM accuracy limitation discussed above.

Thus, what is needed is a method to determine linearity which is less costly and time consuming than the cross-section approach and which is more accurate across a wide range of critical dimensions

SUMMARY OF THE INVENTION

These and other problems are generally solved or circumvented, and technical advantages are generally achieved, by preferred embodiments of the present invention which measures the linearity of a pattern printed on a semiconductor wafer having a photoresist layer into which the pattern, having a plurality of pattern feature, is transferred and having a plurality of layers located beneath the photoresist layer. In one preferred embodiment of the present invention, the method comprises determining an expected pattern edge for each of the plurality of pattern features from a design criteria, formulating measuring patterns for each of the plurality of pattern features, magnifying the semiconductor wafer, analyzing the magnified semiconductor wafer in a top down view, measuring the dimensions of each of the plurality of pattern features using the measuring patterns, and determining the linearity of the pattern utilizing the dimensions of each of the plurality of pattern features.

One of the advantages of a preferred embodiment of the present invention is that the semiconductor wafer is not destroyed during the test for linearity because the wafer is not cut or manipulated in a manner that would result in the wafer being unusable as a finished product.

Another advantage of a preferred embodiment of the present invention is that the method of the present invention is more cost effective than the conventional cross section approach because the wafer is not destroyed resulting in scrap materials, nor is money spent on the process of cutting the wafer.

Yet another advantage of a preferred embodiment of the present invention is that the measuring process is more time efficient because the wafer can be viewed in tact under the top-down scanning electron microscope.

Furthermore, a preferred embodiment of the present invention has the advantage of higher accuracy because the edge location of the photoresist lines can be more easily discerned.

The foregoing has outlined rather broadly the features and technical advantages of the present invention in order that the detailed description of the invention that follows may be better understood. Additional features of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawing, in which.

DETAILED DESCRIPTION OF THE PREFERRED EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

Figure 1:
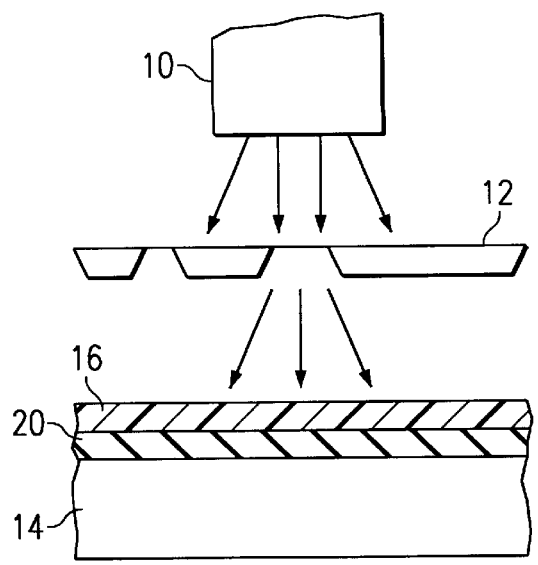
FIG. 1 is a diagram of the photolithography process of semiconductor wafer fabrication.

Referring now to the figures, FIG. 1 illustrates an apparatus for photolithographically printing a pattern onto a semiconductor wafer. The apparatus comprises a light source 10, a mask 12, a wafer 14 on which has been formed an oxide layer 20 and a photoresist layer 16. The light source 10 provides exposing radiation (high intensity light) that is used to form the pattern on the photoresist layer 16. It should also be appreciated that the exposing radiation needed to form the pattern on the photoresist layer 16 can also be produced from other sources including, but not limited to, electrons, x-rays, or ions. The light source 10 illuminates the mask 12 which has a design pattern printed thereon. The mask 12 is positioned above the wafer 14 such that the light shown on the photoresist layer 16 is defined by the design pattern on the mask 12. The photoresist layer 16 of the wafer 14 then contains the design pattern on the mask 12. Thus, a printed pattern results on the wafer 14.

Figure 2:
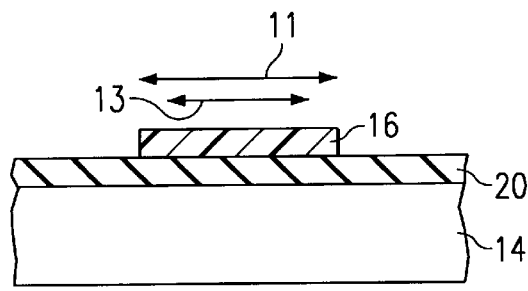
FIG. 2 is a cross section view of a semiconductor wafer with a transferred photoresist line.

In transferring the pattern from the mask onto the wafer 14, some shifting may occur due to various reasons including 2-dimensional proximity effects and 2- or 3-dimensional scaling effects for larger dimensions. These effects result in the printed pattern deviating in design from the corresponding pattern on the mask 12 as shown in FIG. 2. As illustrated, a photoresist layer 16 has been formed atop an oxide layer 20, which oxide is formed on the top surface of semiconductor substrate 14. The photoresist layer 16 has been exposed and patterned using well-known photolithography processes. An undesirable artifact of the photolithographic process is that certain critical dimensions of the desired pattern are not reproduced exactly on the photoresist layer. This is illustrated by comparing line 11, which illustrates the intended dimension of the feature, with line 13, which shows the actual dimension of the resulting feature on the photoresist layer 16 once the photoresist has been exposed. These deviations between the desired pattern and the resulting pattern can degrade device performance. This is particularly so in typical semiconductor process flows wherein pattern features in one layer must be carefully aligned with pattern features formed in underlying layers. To some extent, these deviations can be compensated for by careful photomask design to minimize or offset the effect of optical deviations during the exposure step. Thus, there is a need for measuring and testing the linearity of a photoresist pattern in order to be able to make appropriate corrections to the pattern on the mask which result in an greatly improved accuracy of the actual photoresist edge location compared to the intended or designed photoresist edge location.

Figure 3:
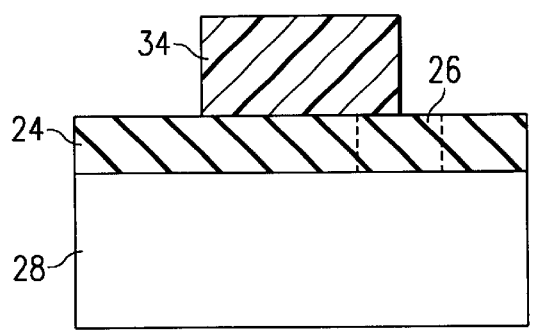
FIG. 3 illustrates a semiconductor wafer utilizing an embodiment of the present invention.

Certain features of a preferred embodiment of the present invention will be described with reference to FIGS. 3 and 4 which illustrate in cross sectional view and plan view, respectively, a semiconductor substrate 28 upon which has been formed a first layer 24. First layer 24 contains a measuring pattern 26, which will be used in measuring critical dimensions of the patterned photoresist feature 34, as will be described below. For generating the measuring pattern 26, well-known semiconductor processes might be applied like shallow trench formation in Silicon 28. A photoresist layer has been formed over layer 24, and has been exposed and patterned using well-known photolithography and photoresist development processes, resulting in photoresist feature 34. It is desirable to measure the critical dimensions of photoresist feature 34 to ensure proper alignment and sizing.

Figure 4:
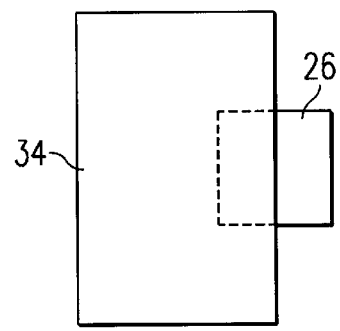
FIG. 4 is a top view of a pattern printed on a semiconductor wafer.

FIG. 4 illustrates the relationship of measuring pattern 26 and photoresist feature 34. In top view, the measuring pattern 26 consists of Silicon lines surrounded by e.g. Silicon Oxide (Shallow Trench Isolation area). The measuring pattern 26 has been formed in underlying layer 24 in a previous process step. From the plan view, it is apparent that the photoresist feature 34 to be measured overlaps the underlying measuring pattern 26 at one edge of the photoresist feature 34. It should be appreciated by one skilled in the art that photoresist feature 34 may be one of many features in the printed pattern.

Figure 5:
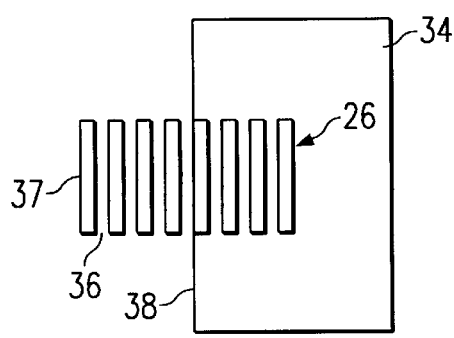
FIG. 5 is the preferred embodiment of the present invention.

In one embodiment of the present invention, the measuring pattern 26 is a series of parallel lines which are printed parallel to a first edge 38 of the pattern feature 34 as illustrated in FIG. 5. The series of parallel lines 26 preferably comprise eight equally spaced lines 37 which form seven spaces 36 therebetween. The series of parallel lines 26 can be used to delineate the amount of shift of a pattern feature 34 or feature edge 38, from its expected location on the semiconductor wafer (not shown). The spaces 36 (or lines) define a shift unit which is equal to the pitch of the lines (or width of the spaces 36). The pitch may be 0.24 to 0.34 microns, but is preferably less than 0.5 microns to provide the most accuracy. The series of parallel lines 26 are placed such that the expected edge 38 of the pattern feature 34 is in the center of the series of parallel lines 26. As such, four of the lines 37 should be visible and four of the visible lines 37 should be obscured if feature 34 is exactly aligned. The series of parallel lines 26 are placed such that a shift in either the left of right direction can be readily detected and measured by simply noting the number of additional lines 37 that are visible (or obscured) using a low magnification in the scanning electron microscope. Subsequently, a high magnification view of the photoresist edge location is taken while two lines of the measurement pattern 26 and the photoresist edge are visible. It should be appreciated by those skilled in the art that the selection of the number of lines in the series and the placement of the series with respect to the expected pattern edge is only constrained by the physical dimensions of the substrate and the pattern features printed on the substrate to provide the accuracy required. The accuracy of the edge location measurement, then, no longer depends on the size of the pattern feature 34 but is dictated by the pitch of the measuring pattern.

Figure 6:
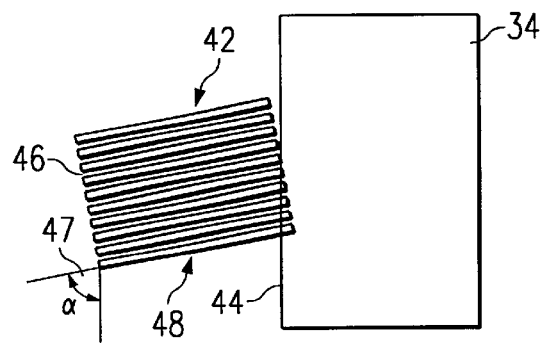
FIG. 6 is another preferred embodiment of the present invention.

Another embodiment is illustrated in FIG. 6. The embodiment comprises a series of parallel lines 42 which are placed at an angle 46 to an edge 44 of the pattern feature 34. Note that in this embodiment, only a portion of the parallel lines are obscured by the pattern feature. The series of parallel lines 42 form a series of spaces 46 between the series of parallel lines 42. The angle of orientation 47 is defined as the angle between the edge 44 defined along an axis (here, the y-axis) and a position 48 after rotating the measuring pattern away from the axis. The angle 47 is preferably between 80 and 85 degrees to provide the accuracy needed for smaller pattern features. The pitch of the series of parallel lines 42 is still defined by the width of the spaces 46 between the series of parallel lines 42. However, the shift unit is now equal to the product of the pitch and the cosine of the angle 47. For example if the pitch of the series of parallel lines is 0.5 micron and the angle 47 is 85° then the shift unit is equal to 0.5 micron x cos (85°) or 0.4 micron. Even though the lines have a pitch of 0.5 micron, the resolution of the pattern is 0.4 micron. In other words, each additional line that is obscured by the pattern edge corresponds to another 0.4 micron of pattern edge shift. Thus, this embodiment provides the necessary accuracy for photoresist edge location measurements of smaller dimensions.

Figure 7:
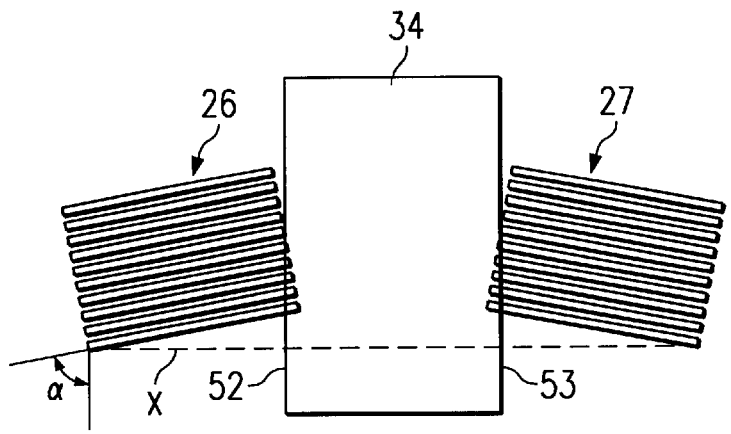
FIG. 7 is another embodiment of the present invention.

A third embodiment shown in FIG. 7 illustrates the use of two measuring patterns 26 and 27 as described above. By using two measuring patterns 26 and 27 at the two photoresist edges 52 and 53, both photoresist edges 52 and 53 can be located with sufficient accuracy and elimination of overlay influences achieved. If A denotes the shift of edge 52 in reference to measurement pattern 26, and B denotes the shift of edge 53 in reference to measurement pattern 27, the change in dimension of the photoresist line 34 is given by B-A, if all values are determined in reference to the x-coordinate indicated in FIG. 7. An important feature of this invention is the fact that by applying the measurement patterns in an underlying layer 24 the accuracy of the edge location determination is decoupled or independent from the photoresist pattern dimension which is to be measured. Hereby, photoresist patterns with dimensions up to several hundred microns are possible to be measured.

Figure 8:
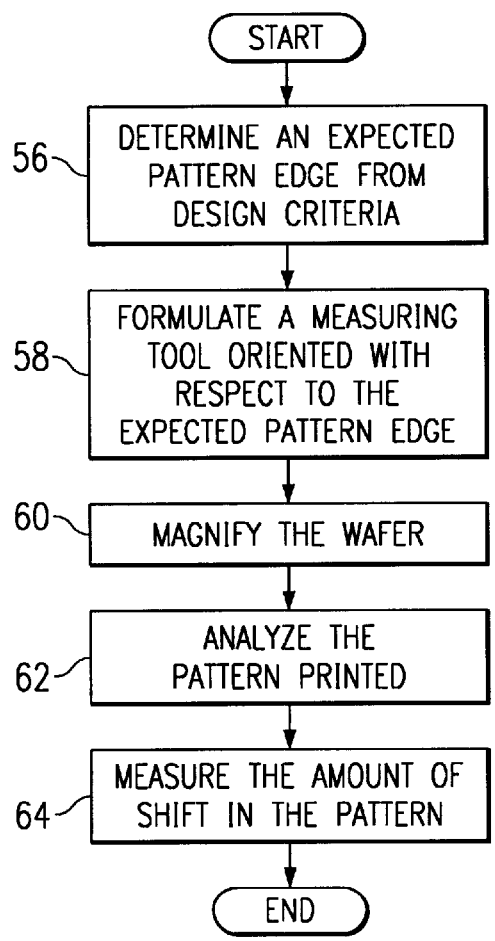
FIG. 8 is a flow chart of a method of utilizing the various embodiments of the present invention.

A method of utilizing the various embodiments of the present invention is illustrated by the flowchart in FIG. 8. The method comprises, at steps 56 and 58, determining at least two expected pattern edges for a pattern feature from a design criteria and formulating a measuring pattern which is oriented with respect to at least one of the expected pattern edges. The formulation of the measuring pattern includes printing the measuring pattern at a layer beneath the layer on which a pattern to be measured is printed. At step 60 the semiconductor wafer containing the measuring pattern and pattern to be measured is magnified. The edge locations of the pattern on the wafer are then analyzed in a high-magnification top down view at step 62. At step 64 the linearity of the pattern is measured by determining the amount of shift of the edge locations. It should be noted that the accuracy of the measurement is dependent on the pitch and the angle function as explained previously. By reiterating the steps indicated in the flowchart of FIG. 8 for different pattern features and dimensions (e.g. between 0.1 $\mu$m and 300 $\mu$m) the photoresist linearity behavior can be determined for an extraordinarily wide range.

While this invention has been described with reference to illustrative embodiments, this description is not intended to be construed in a limiting sense. It should be understood that the present invention is discussed relative to a single pattern feature (photoresist line), however on a wafer containing a pattern having many features, the present invention may be used with each of the many features. Various modifications and combinations of the illustrative embodiments, as well as other embodiments of the invention, will be apparent to persons skilled in the art upon reference to the description. It is therefore intended that the appended claims encompass any such modifications or embodiments.

Moreover, as one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for measuring the linearity of a pattern printed on a semiconductor wafer having a photoresist layer into which the pattern is transferred and having at least one layer located beneath the photoresist layer, the pattern having a plurality of pattern features with at least two edges, the method comprising:

determining expected pattern edges for each of the plurality of pattern features from a design criteria;

formulating measuring patterns on the semiconductor wafer in the at least one layer located beneath the photoresist layer, each measuring pattern corresponding to one of the plurality of pattern features and comprising a series of parallel lines having a pre-determined pitch and oriented at an angle with respect to at least one of the expected pattern edges of the corresponding pattern feature;

magnifying the semiconductor wafer;

analyzing the magnified semiconductor wafer in a top down view;

measuring the number of parallel lines in each measuring pattern which are obscured by one of the at least two edges of the corresponding pattern feature; and deriving the linearity of the pattern based upon the number of obscured parallel lines and the pitch of said parallel lines for each measuring pattern.

2. The method of claim 1 wherein the pre-determined pitch is defined as the distance between the second edge of a one of the series of parallel lines and the second edge of another of the series of parallel lines which is adjacent to the one of the series of parallel lines.

3. The method of claim 1 wherein the pre-determined pitch is less than 500 nm.

4. The method of claim 1 wherein the semiconductor wafer is magnified with a scanning electron microscope.

5. The method of claim 1 wherein deriving the linearity of the pattern is accomplished using image analysis software.

6. The method of claim 1 wherein deriving the linearity of the pattern comprises determining the amount of shift of one of the at least two edges of each of the pattern features from the corresponding first expected pattern edge.

7. The method of claim 1 wherein the angle is between 80 and 85 degrees.

8. The method of claim 1 wherein the angle is zero degrees.

9. The method of claim 6 wherein the shift is measured in shift units, each shift unit equal to the product of the pre-determined pitch of the measuring pattern and the cosine of the angle.

10. The method of claim 3 wherein each measuring pattern comprises at least two sets of parallel lines.

11. The method of claim 10 wherein a second expected pattern edge for each of the plurality of pattern features is determined before formulating the measuring pattern on the semiconductor wafer.

12. The method of claim 11 wherein the pre-determined pitch is defined as the distance between the second edge of a one of the parallel lines in a set and the second edge of another of the parallel lines which is adjacent to the one of the parallel lines.

13. The method of claim 12 wherein deriving the linearity of the pattern comprises determining the amount of shift of each of the at least two pattern edges from each of the at least two expected pattern edges.

14. The method of claim 13 wherein the one of the at least two sets of parallel lines is oriented with respect to one of the at least two expected pattern edges and another of the at least two sets of parallel lines is oriented with respect to the other of the at least two expected pattern edges.

15. The method of claim 14 wherein the angle is between 80 and 85 degrees.

16. The method of claim 14 wherein the angle is zero degrees.

17. The method of claim 14 wherein the shift is measured in a shift unit equal to the product of the pre-determined pitch and the cosine of the angle.

18. An apparatus for measuring the linearity of a pattern feature formed in a photoresist layer formed atop a semiconductor substrate, the pattern feature having at least two pattern edges, the apparatus comprising:

a semiconductor substrate;

a first layer formed atop the semiconductor substrate, the first layer including a measuring pattern comprising a series of parallel lines having a line width defined by a first and a second edge and having a pre-determined width; and a photoresist layer formed atop the first layer having a pattern feature formed therein;

wherein the pattern feature obscures one or more of the parallel lines and the linearity of the pattern feature can be determined from the non-obscured parallel lines.

19. The apparatus of claim 18 wherein the series of parallel lines are at a pitch less than 500 microns.

20. The apparatus of claim 19 wherein the measuring pattern is utilized to determine the amount of shift of at least one of the at least two pattern edges from a pre-determined location.

21. The apparatus of claim 20 wherein the shift is measured in a shift unit equal to the product of the pre-determined pitch and the cosine of an angle of orientation between the pattern edges and the parallel lines.

22. The apparatus of claim 21 wherein the angle of orientation is between 80 and 85 degrees.

* * * * *